United States Patent
Paritosh

[19]

[11] Patent Number: 6,121,462

[45] Date of Patent: Sep. 19, 2000

[54] SUBSTITUTIONS ON AZETIDINES BY ACYLATIVE DEALYLATION WITH LEWIS ACID CATALYSIS

[75] Inventor: Dave Paritosh, Bridgewater, N.J.

[73] Assignee: The United States of America as represented by the Secretary of the Army, Washington, D.C.

[21] Appl. No.: 09/152,716

[22] Filed: Sep. 14, 1998

Related U.S. Application Data

[62] Division of application No. 08/440,947, May 15, 1995, Pat. No. 5,808,099, and a division of application No. 08/440,946, May 15, 1995, and a division of application No. 08/440,945, May 15, 1995, abandoned, and a division of application No. 08/441,511, May 15, 1995, Pat. No. 5,580,988, and a division of application No. 08/441,512, May 15, 1995.

[51] Int. Cl.$^7$ ................................................ C07D 205/00
[52] U.S. Cl. ........................................... 548/952; 548/953
[58] Field of Search ..................................... 548/952, 953

[56] References Cited

U.S. PATENT DOCUMENTS 5,580,988 12/1996 Dave ........................................ 548/953

*Primary Examiner*—Johann Richter
*Assistant Examiner*—Joseph Murray
*Attorney, Agent, or Firm*—John F. Moran; John E. Callaghan

[57] ABSTRACT

The invention is a process for the modification or substitution of aza substituted azetidines through acylative dealkylation.

17 Claims, 1 Drawing Sheet

6,121,462

SUBSTITUTIONS ON AZETIDINES BY ACYLATIVE DEALYLATION WITH LEWIS ACID CATALYSIS

STATEMENT OF GOVERNMENT INTEREST

The invention described herein may be manufactured, used and licensed by or for the United States Government for governmental purposes without the payment to us of any royalties thereon.

STATEMENT OF RELATED APPLICATIONS

This application is a division of the U.S. Patent Applications described below. The subject matter of this application is disclosed in the several applications and in the copending applications that were included by reference therein. The applications are:

DAR 4-94A Ser. No. 08/440,947 filed May 15, 1995 now U.S. Pat. No. 5,808,099,
DAR 4-94B Ser. No. 08/440,946 filed May 15, 1995, pending,
DAR 4-94C Ser. No. 08/440,945 filed May 15, 1995 now abandoned,
DAR 4-94D Ser. No. 08/441,511 filed May 15, 1995 now U.S. Pat. No. 5,580,988,
DAR 4-94E Ser. No. 08/441,512 filed May 15, 1995, pending.

BACKGROUND OF INVENTION

This invention relates to processes for modifying or substituting groups on azetidines, particularly replacing N-tertiary butyl groups with more easily removed groups. The azetidine ring was first identified in 1888 but has not received much interest because of the difficulties in preparing the compounds and the poor yields associated with the various preparative methods. There are important areas of chemistry and biochemistry arising from the azetidinyl structure which are not researched because the compounds can not be synthesized. Aziridines have biological activity. L-azetidine-2-carboxylic acid is an amino acid that can replace 1-proline in protein synthesizing systems. Polyoximic acid includes an azetidinyl ring and this acid is a constituent of an antibiotic nucleoside tripeptide, polyoxin A.

The aza substituted, 3-substituted azetidines are especially difficult to prepare. The most available member is the N-tertiary butyl,3-hydroxyazetidine. The next most available other member is N-benzhydryl,3-hydroxyazetidine. Other than these members, attempts to prepare the amines, amides, sulfinamides, and others lead to linear polymers, eight member rings, etc. There is a powerful tendency for the four member ring to open and thus the azetidinyl structure is not preserved. When the 3-substituent is to be modified from the hydroxyl group, it generally is converted via mesylate or chloride intermediates. In order to convert the aza group it is usual to proceed by a benzhydryl group as the aza substituent and then replace it with the corresponding hydrogen to the secondary amine. This is then modified to the corresponding target group such as alkyl, acetyl, sulfonyl, haloalkyl, nitrogen, etc. It is very desirable to provide processes which will make substituted aza azetidines with a wide variety of substituents and under mild conditions.

SUMMARY OF INVENTION AND FIGURES

Overall, the processes of this invention for preparing substituted or modified azetidines are advantageous in that the reaction conditions give improved yields and readily recoverable products. This invention uses a Lewis acid as a catalyst in processes which modify or substitute aza substituted azetidines. It is particularly noteworthy that it works very well with N-tertiarybutyl groups because this shows that the ring will not be opened even though a relatively stable group is removed. The Figures illustrate the several process sequences according to the invention.

DETAILED DESCRIPTION OF THE INVENTION

The practice of the invention and the processes and reaction conditions of the steps of the invention are further described by reference to the following detailed description.

The overall mechanism of the invention appears to be that the Lewis acid forms a complex at the aza nitrogen of the ring system. This leads to the initial aza substituent leaving the compound and a complexed secondary amine is formed at the aza nitrogen. If the reaction were to stop at this point, the free amine would be the reaction product. In the presence of electrophillic compounds, the new substituent forms a bond with the aza nitrogen which disassembles the complex and releases the Lewis acid for reaction with another azetidine. This accounts for the catalytic action of the Lewis acid and has opened up a vast new availability of azetidine compounds. Under these reaction conditions it takes less energy to remove a group such as tertiary butyl than it does to break the ring. This applies to other bulky alkyl and aryl groups such as benzyl, benzhydryl and trityl, which have the monoaryl, diaryl and triaryl groups attached to a tertiary carbon.

With the invention, the aza nitrogen group can be modified and the ring substituents can be modified. It is a versatile synthesis tool where the initial aza substituent can be replaced and then the other ring atoms can be modified or substituted. In addition there can be further substitution of the group at the aza nitrogen. For example, the aza acetyl group can be replaced with a nitro group. Among the important compounds produced by the process are the N-acetyl, 3-substituted azetidines. The substituents of the tertiary carbon can be unsaturated alkyl such as vinyl.

Figure 1:
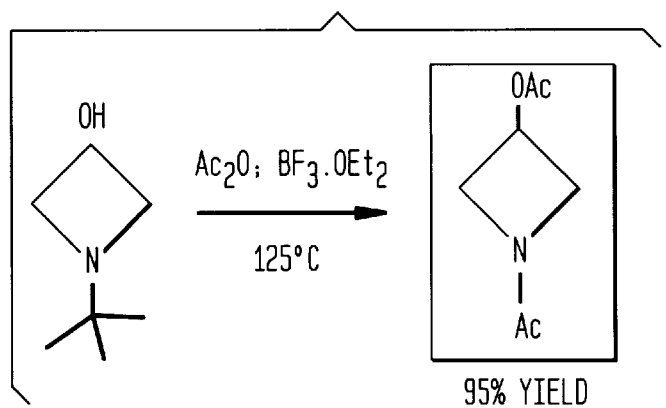

The general reaction is illustrated in FIG. 1. The azetidine is the N-tertiarybutyl,3-hydroxyazetidine. This represents the most readily available azetidine. The tertiary butyl group forms very stable carbocations. In the order of stability, the aza nitrogen is connected to two carbon atoms in the ring. The comparative stability is that of the aza substituent versus the bonds of the ring carbons to the aza nitrogen. The ring will break if the bonds of the ring carbons are less stable than the aza substituent. As initial substituents on the aza nitrogen, the most common groups are isopropyl, tertiary butyl, and benzhydryl. It can be seen that an important advantage of the invention is that it overcomes the stability of the aza subsequent as a negative factor when conducting modifications and substitutions of the azetidine.

The reaction can be conducted in the presence of a solvent. Acetic anhydride is both a solvent and a reactant. Once the initial subsequent is removed from the aza position, electrophillic compounds can then form a bond with the aza nitrogen. Other systems will use inert solvents and reactants. The acetyl function is desirable because it can be replaced with other groups. Other desirable electrophillic compounds are acid halides and haloalkyl acids. At least for the first replacement of the initial aza substituent, the replacement group is desirably easily hydrolysable such as acyl, sulfonyl, haloacyl, nitro. The ultimate azetidine compound can have groups more tailored to the end use such as nitro or trifluoroacyl.

For this invention, the Lewis acid is a non-protic acid and can be in the form of a complex with an oxygen compound. The preferred members are those having metals selected from aluminum, boron, tin, zinc and iron. The most available members are the halides and alkyls. Particular examples are boron trifluoride, stannic chloride, zinc chloride, ferric chloride and ferric chloride. The ether complexes can be used in place of the acid itself.

The reaction temperature is not itself critical. The temperature range of about 70 degrees C. to about 125 degrees C. is suitable for reaction times of several hours. Lower temperatures increase the reaction time.

The product of the reaction is N-acetyl,3-acetoxyazetidine. The tertiary butyl group at the aza nitrogen has been replaced by the acetyl group. The medium hydrolyzed the 3-hydroxy to the acetoxy group. This compound is a versatile intermediate for a number of other difficulty accessible azetidinyl compounds. The 3-acetoxy function can be cleanly hydrolyzed to hydroxyl under mild conditions to give N-acetyl,3-hydroxyazetidine. This alcohol function can be oxidized to the ketone. Oxidation agents such as pyridinium chlorochromate are effective. The ketone is an example of a 3-keto azetidine that has an electron withdrawing group at the aza nitrogen; the stability of the ketone is enhanced.

The N-acetyl,3-azetidinone may be reacted with hydroxyl amine to produce the N-acetyl,3-oximido azetidine. This has acetyl and oximido groups that can be nitrated to 1,3,3-trinitroazetidine. An advantage is that the three nitro groups are added to the azetidine at the final step of the process.

Another synthesis starts again with the N-acetyl,3-acetoxy azetidine. A nitration converts the N-acetyl to N-nitro and a subsequent hydrolysis converts the 3-acetoxy to 3-hydroxyl. Then, the 3-hydroxyl is oxidized to the 3-ketone. The result is a new procedure to produce N-nitro, 3-azetidinone. The ketone can be converted to the oxime and then the compound can be nitrated to TNAZ.

These sequences of modifications and substitutions are illustrating the power of the procedure of the invention to lead to new classes of compounds and to make other compounds available at reasonable costs.

Figure 2:
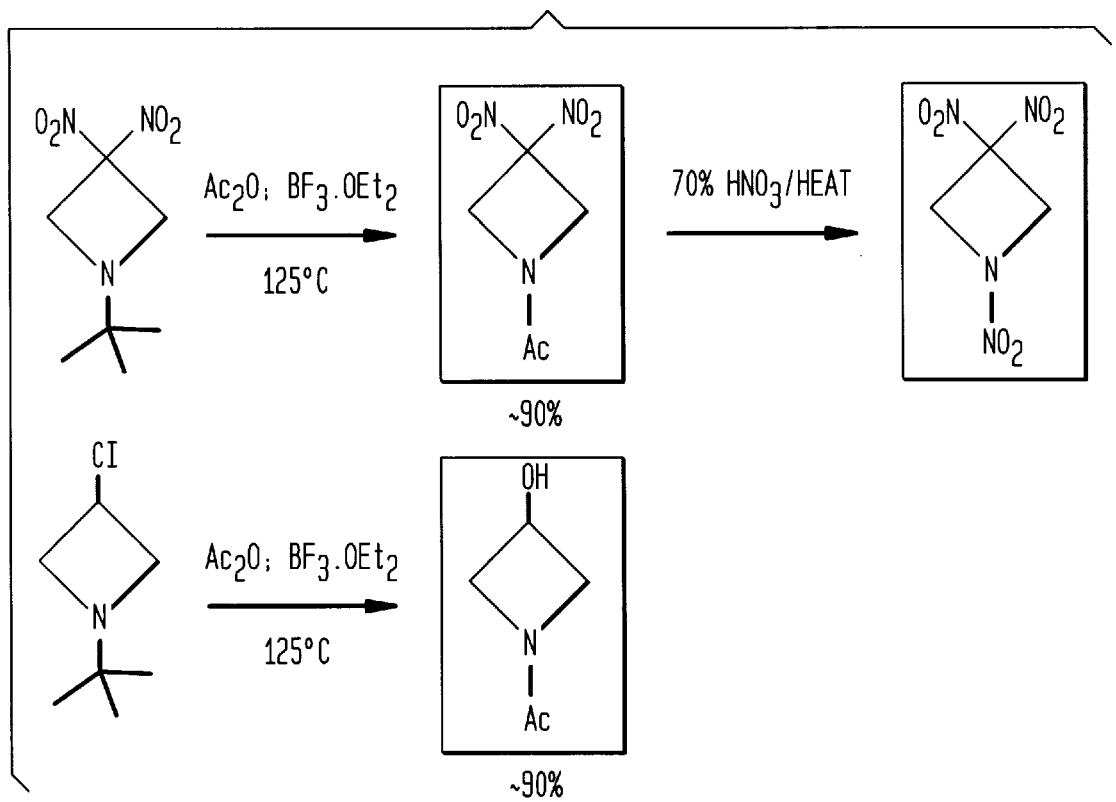

FIG. 2 illustrates the use of N-tertiarybutyl azetidines having other 3-substituents in the practice of the invention. These specific examples are shown to illustrate methods which also can produce TNAZ. The azetidines of the invention can have substituents at the 2 position of the ring. The substituents can be selected from hydroxyl, acyloxy, halo, cyano, and ester groups.

The upper reaction scheme is the conversion of the N-tertiarybutyl,3,3 dinitroazetidine to the N-acetyl, 3,3 dinitroazetidine. The reaction conditions are a catalytic amount of boron trifluoride etherate as the Lewis acid and acetic anhydride as the solvent-reactant. The temperature is 125 degrees C. As shown there was about a 90% yield. The compound is nitrated with 70% nitric acid and heated to give TNAZ.

The lower reaction scheme illustrates the N-tertiarybutyl, 3-chloroazetidine being converted to the N-acetyl,3-chloroazetidine. The yield is 90% under the reaction conditions shown. On treatment with aqueous alkali, the N-acetyl,3-chloroazetidine splits out the acetoxy and chloride and is cyclized to azabicylobutane. This is another route to TNAZ.

During the reactions described above selected compounds were be identified and followed by NMR. 1H and 13C NMR were used for following N-acetyl,3-azetidinone; N-nitro,3-acetoxyazetidine and N-nitro,3-hydroxyazetidine. 1H NMR was used for N-acetyl,3-chloroazetidine. It should be understood that other compounds of interest that have been identified in the reactions are N-acetyl,3-cyanoazetidine, and N-acetoxy,3-chloroazetidine. Both of the acetoxy and cyano functions of N-acetyl,3-cyanoazetidine can be hydrolyzed to provide the 3-azetidino acetic acid. It can be seen that the above reactions apply the principles of acylative dealkylation to substitution of aza substituted azetidines. The catalytic action of the Lewis acid in forming the secondary amine complex appears to be the key to the reactions that are now possible through the invention.

It is intended that the invention includes the equivalent compounds, products, reaction conditions, reaction steps, reaction processes and variations of such equivalents as are commonly practiced in this field as well as the specific embodiments described above.

I claim:

1. A process for modifying an aza substituted azetidine by acylative dealkylation with a catalytic amount of a Lewis acid, said process comprising: forming a complex between the Lewis acid and an azetidine having an initial aza substituent, removing the initial aza substituent and replacing the same with an acyl group.

2. The process of claim 1 where the initial substituent is selected from groups containing at least three carbon atoms.

3. The process of claim 1 where the initial aza substituent is a group having carbon and hydrogen atoms.

4. The process of claim 1 where the initial aza subsequent is selected from groups having at least three carbon atoms and the carbon attached to the nitrogen atom is a secondary or tertiary carbon.

5. The process of claim 1 where the initial aza substituent is tertiary butyl.

6. The Process of claim 1 where the initial aza substituent is benzhydryl.

7. The Process of claim 1 where the initial aza substituent is tertiary octyl.

8. The process of claim 1 where the Lewis acid is selected from boron trifluoride and complexes thereof.

9. The process of claim 1 where the initial aza substituent is tertiary butyl and the Lewis acid is selected from boron trifluoride and complexes thereof.

10. The process of claim 1 where the azetidine having the initial substituent is tertiary butyl azetidine.

11. The process of claim 1 where the azetidine having the initial substituent is a 3-substituted tertiary butyl azetidine.

12. The process of claim 1 where the azetidine having the initial substituent has tertiary butyl as the initial subsequent and has one or more other substituents selected from hydroxyl, acyloxy, halo, haloalkyl, cyano, ester and nitro groups.

13. The process of claim 1 where the azetidine having the initial substituent has tertiary butyl as the initial subsequent and has one or more other substituents at the three position selected from hydroxyl, acyloxy, halo, haloalkyl, cyano, ester and nitro groups.

14. The process of claim 1 where the Lewis acid is selected from aluminum trichloride, boron trifluoride, zinc chloride and complexes thereof.

15. A process catalyzed by a Lewis acid to produce an aza substituted azetidine comprising: combining an azetidine having an initial aza substituent and a Lewis acid to form a complex, removing the initial aza substituent and adding a substituent at the aza position that is different from the original substituent, the initial aza substituent being capable of forming stable carbocations.

16. The process of claim 15 where the product is a substituted azetidine with an acyl group at the aza position and at least one other substituent on the carbon atoms of the azetidine ring.

17. The process of claim 1 where the substituted azetidine product has an aza acetyl group and an acetoxy group at the 3-position.

* * * * *

UNITED STATES PATENT AND TRADEMARK OFFICE
CERTIFICATE OF CORRECTION

PATENT NO : 6,121,462
DATED : September 19, 2000
INVENTOR(S): Paritosh Dave

It is certified that error appears in the above-identified patent and that said Letters Patent are hereby corrected as shown below:

On the title page heading line, "Paritosh" has been deleted, and --Dave-- was inserted to replace it.

On the title page item [75], the name "Dave Paritosh" has been deleted, and replaced with --Paritosh Dave--.

Signed and Sealed this

Twenty-fourth Day of April, 2001

*Attest:*

NICHOLAS P. GODICI

*Attesting Officer*     *Acting Director of the United States Patent and Trademark Office*